United States Patent
Visvanathan et al.

(10) Patent No.: US 9,955,880 B2
(45) Date of Patent: May 1, 2018

(54) ESTIMATING PHYSIOLOGICAL PARAMETERS

(71) Applicant: Tata Consultancy Services Limited, Mumbai (IN)

(72) Inventors: Aishwarya Visvanathan, Whitefield (IN); Arpan Pal, Kolkata (IN); Aniruddha Sinha, Kolkata (IN); Rohan Banerjee, Kolkata (IN); Anirban Dutta Choudhury, Kolkata (IN); Aditi Mishra, Kolkata (IN); Avik Ghose, Kolkata (IN)

(73) Assignee: Tata Consultancy Services Limited, Mumbai (IN)

(*) Notice: Subject to any disclaimer, the term of this patent is extended or adjusted under 35 U.S.C. 154(b) by 574 days.

(21) Appl. No.: 14/665,657

(22) Filed: Mar. 23, 2015

(65) Prior Publication Data

US 2016/0113531 A1   Apr. 28, 2016

(30) Foreign Application Priority Data

Oct. 27, 2014   (IN) .......................... 3396/MUM/2014

(51) Int. Cl.
*G06K 9/00* (2006.01)
*A61B 5/024* (2006.01)
(Continued)

(52) U.S. Cl.
CPC ........ *A61B 5/02416* (2013.01); *A61B 5/0082* (2013.01); *A61B 5/02438* (2013.01); *A61B 5/14551* (2013.01); *A61B 2560/0238* (2013.01)

(58) Field of Classification Search
CPC .............. A61B 5/0082; A61B 5/02416; A61B 5/02438; A61B 5/14551; A61B 2560/0238
See application file for complete search history.

(56) References Cited

U.S. PATENT DOCUMENTS

| 8,740,806 B2 * | 6/2014 | Parfenova ............ A61B 5/4818 600/484 |
| 2004/0247154 A1 * | 12/2004 | Bodo .................... G06T 1/0085 382/100 |

(Continued)

OTHER PUBLICATIONS

Wieringa et al (Contactless Multiple Wavelength Photoplethysmographic Imaging: A first step toward "SpO2 Camera" Technology, Annals of Biomedical Engineering, vol. 33, No. 8, Aug. 2005, pp. 1034-1041).*

*Primary Examiner* — Amara Abdi
(74) *Attorney, Agent, or Firm* — Schwegman Lundberg & Woessner, P.A.

(57) ABSTRACT

A physiological parameter measurement device comprising a processor and a video processing module coupled to the processor to divide each of a plurality of frames of a video into a plurality of blocks, where the video is of a body part of a subject whose physiological parameter is to be determined. The video processing module further is to select a block having highest peak signal to noise ratio (PSNR) from amongst the plurality of blocks. Further, the video processing module is to extract a photoplethysmogram (PPG) signal from the video based on a block identifier associated with the block. The physiological parameter measurement device further comprises a signal enhancement module coupled to the processor, to process the PPG signal to obtain an enhanced PPG signal for determining a value of the physiological parameter for the subject.

14 Claims, 2 Drawing Sheets

(51) Int. Cl.
*A61B 5/1455* (2006.01)
*A61B 5/00* (2006.01)

(56) References Cited

U.S. PATENT DOCUMENTS

2013/0294505 A1* 11/2013 Kirenko ........... H04N 19/00006
              375/240.02
2016/0235312 A1* 8/2016 Jeanne .................... A61B 5/72

* cited by examiner

ESTIMATING PHYSIOLOGICAL PARAMETERS

CLAIM OF PRIORITY

This application claims the benefit of priority of India Patent Application Serial No. 3396/MUM/2014, filed on Oct. 27, 2014, the benefit of priority of which is claimed hereby, and which is incorporated by reference herein in its entirety.

TECHNICAL FIELD

The present subject matter relates, in general, to photoplethysmography and, particularly but not exclusively, to estimating physiological parameters of a subject based on photoplethysmography.

BACKGROUND

With the advancement in technology, (PPG) has been developed for measuring physiological parameters, such as heart rate of individuals. The PPG is a non-intrusive optical technique and involves use of light for measuring change in blood volume of the individual. Based on the measurement, a PPG signal indicative of changes in blood volume may be obtained. The PPG signal may then be used for estimating the physiological parameters associated with the individual.

BRIEF DESCRIPTION OF DRAWINGS

The detailed description is described with reference to the accompanying figures. In the figures, the left-most digit(s) of a reference number identifies the figure in which the reference number first appears. The same numbers are used throughout the drawings to reference like features and components.

DETAILED DESCRIPTION

Figure 1:
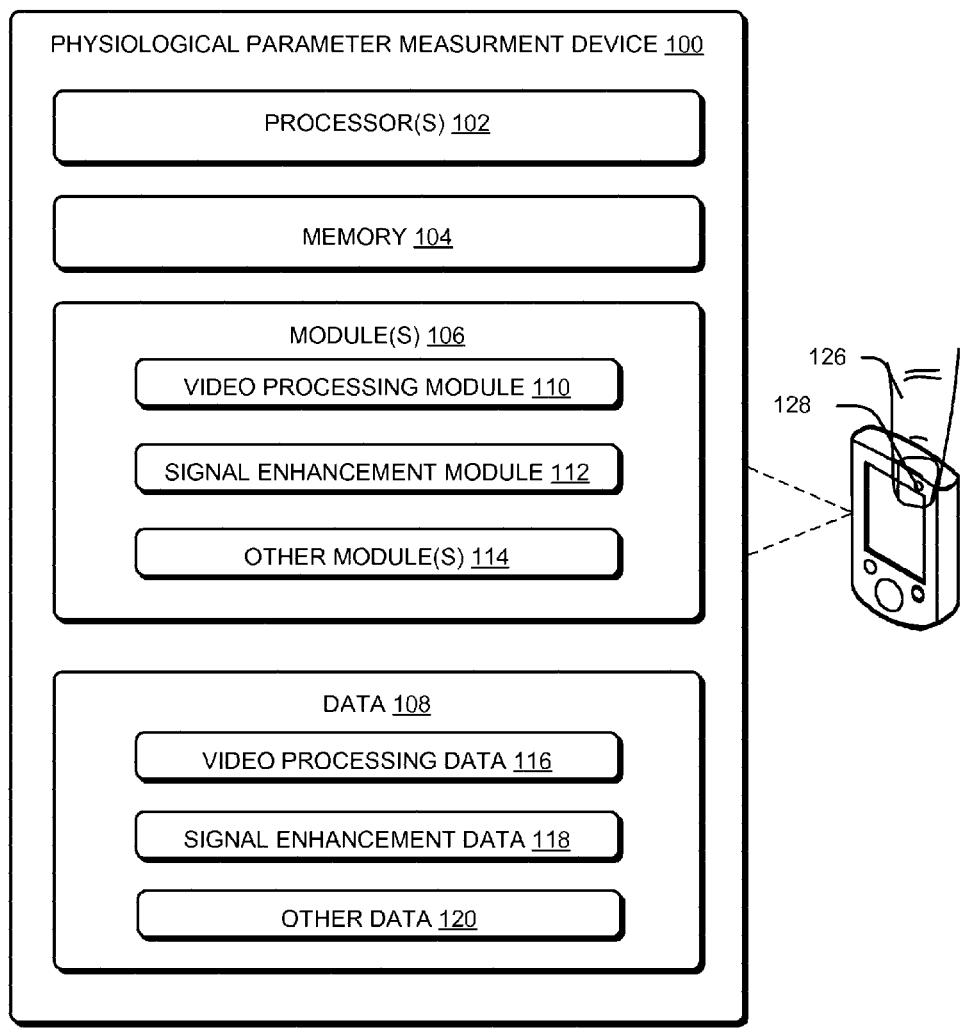
FIG. 1 illustrates a physiological parameter measurement device for determining physiological parameter associated with a subject, in accordance with an implementation of the present subject matter.

The present subject matter relates to determining physiological parameter of a subject, for example, an individual, using photoplethysmography (PPG). The PPG is a non-intrusive optical technique used for measuring physiological parameters, such as heart rate of the subject.

In PPG, a PPG signal associated with an individual is recorded using standard medical grade equipment. The PPG signal is indicative of volumetric changes in blood flow of the individual and is used for determining the heart rate of the individual. However, such medical equipment are costly to procure and thus, individuals who seek to get their heart rate measured on a periodic basis may have to repeatedly visit clinics with such medical equipments for getting their heart rate measured. Further, the medical equipments may only be operated by a skilled personal thereby limiting the operational utility of the medical equipments.

With the development of technology, individuals can nowadays measure their physiological parameters using smart phones equipped with a light source, such as a light emitting diode (LED) flash and a video capturing device, for example, a camera. For estimating a physiological parameter of the individual using a smart phone, a video of a body part, typically a finger, of the individual is recorded using the camera of the smart phone with LED flash ON. The video is then processed for extracting a PPG signal associated with the individual. Based on the PPG signal, the physiological parameter of the individual is estimated.

In a conventional approach for extracting PPG signal from the video, a central block of predefined dimensions is selected from each frame of the video. The central block may be understood as a block located in the center of the frame. Thereafter, based on a mean value corresponding to each of the central blocks the PPG signal is extracted. Owing to the location of the flash with respect to the camera, the PPG signal obtained based on the central blocks may be of a poor quality. For instance, the flash may cause saturation of the pixels of the frame which are nearer to the flash. Thus, the PPG signal extracted from such a region, for example, the central block, may be of a poor quality. Therefore, any physiological parameter determined based on such a PPG signal may not reflect an accurate value of the physiological parameter. Additionally, skin tone of the individual may also affect the quality of the PPG signal obtained. For example, in case of fair skinned individuals, most of the light from the LED flash is reflected back and the video recorded is high in intensity. Thus, the PPG signal extracted from such a video may be of a poor quality and may not be useful for estimating the physiological parameter of the individual.

The present subject matter describes systems and methods for estimating physiological parameter of a subject. According to an aspect, each of a plurality of frames corresponding to a video of a body part of the subject may be divided into a plurality of blocks. Thereafter, the PPG signal based on which the physiological parameter of the subject may be determined may be extracted from the video based on a block having highest peak signal to noise ratio (PSNR) from amongst the plurality of blocks. The high PSNR indicates that a region of the frame corresponding to the block contains least noise component and thus, the PPG signal extracted based on such a block results in a good quality PPG signal. As a result, an accuracy of determination of the physiological parameter may be increased.

The frames of the video may be divided into the plurality of blocks. In an example, the frames of the video may be divided in a manner such that each of the blocks may be of a same predetermined dimension. In an implementation, a peak signal to noise ratio (PSNR) for each of the blocks may be computed. The PSNR may indicate a level of noise in a region of the frame corresponding to the block. For instance, a block with high PSNR may indicate a region of the frame having less noise component while, a block having low PSNR may indicate a region of the frame having high noise component. Based on the PSNRs of the blocks, the block having the highest PSNR may be selected.

As mentioned above, the PPG signal may be extracted from the video based on the block having the highest PSNR. For extracting the PPG signal, a block identifier associated with the block may be ascertained. The block identifier may be understood as an identifier, for example, a block number or co-ordinates associated with the block, indicative of a region of the frame. In an example, the block identifier may be ascertained using known techniques. On ascertaining the block identifier, a region corresponding to the block identifier is identified in each frame of the video. As the regions correspond to the block identifier, the PSNRs corresponding to such regions may also be high and therefore, may represent a region of the video having least noise component.

Subsequently, the PPG signal may be extracted from the identified regions of the frames of the video. For reasons mentioned above, the PPG signal extracted from such regions may be of good quality and may facilitate determination of the physiological parameter with greater accuracy.

As may be understood, the PPG signal is in frequency domain and a dominant peak in the frequency spectrum of the PPG signal is used for calculating the physiological parameter. In an implementation, the PPG signal may be enhanced for increasing the accuracy of determination of the physiological parameter. For example, the PPG signal may be passed through an adaptive filter, such as a normalized Least Mean Square (NLMS) filter, to obtain a filtered PPG signal having reduced noise. Thereafter, an interpolation technique may be applied to the filtered PPG signal for enhancing the filtered PPG signal. Examples of the interpolation technique may include, but are not limited to, linear interpolation and Jacobsen interpolation. The enhancement of the PPG signal may result in a fine tuned form of the frequency domain representation of the filtered PPG signal. As a result, dominant peak in the frequency spectrum of the PPG signal is easier to determine from the enhanced PPG signal. Thus, enhancement of the PPG signal further increases the accuracy of determination of the physiological parameter.

As will be clear from the foregoing description, selection of the block having the highest PSNR for extracting the PPG signal facilitates in obtaining a good quality PPG signal having less noise component. As a result, physiological parameters determined from such a PPG signal are determined with greater accuracy. Further, in contrast to extracting the PPG signal from the complete video, the PPG signal may be extracted from the video based on the block identifier. As a result, devices having less computational power, such as low processing capability smart phones, may be implemented for extraction of the PPG signal and, in turn, determination of the physiological parameters. Further, the enhanced PPG signal further increases the accuracy of determination of the physiological parameter of the subject.

These and other advantages of the present subject matter would be described in greater detail in conjunction with the following figures. While aspects of described systems and methods can be implemented in any number of different computing systems, environments, and/or configurations, the embodiments are described in the context of the following device(s).

FIG. 1 illustrates a physiological parameter measurement device 100 for determining physiological parameters associated with a subject, in accordance with an implementation of the present subject matter. The physiological parameter measurement device 100, hereinafter referred to as the device 100, can be a handheld device and can include any of the devices, for example, mobile phones, personal digital assistant (PDA), smart phones, or tablet personal computers. In another example, the device 100 may be an electrical device, such as those used in clinical setting for monitoring or estimating the physiological parameters associated with subjects.

In one implementation, the device 100 includes processor(s) 102 and memory 104. The processor(s) 102 may be implemented as one or more microprocessors, microcomputers, microcontrollers, digital signal processors, central processing units, state machines, logic circuitries, and/or any devices that manipulate signals, based on operational instructions. Among other capabilities, the processor(s) 102 is provided to fetch and execute computer-readable instructions stored in the memory 104. The memory 104 may be coupled to the processor(s) 102 and can include any computer-readable medium known in the art including, for example, volatile memory, such as Static Random Access Memory (SRAM) and Dynamic Random Access Memory (DRAM), and/or non-volatile memory, such as Read Only Memory (ROM), erasable programmable ROM, flash memories, hard disks, optical disks, and magnetic tapes.

Further, the device 100 may include module(s) 106 and data 108. The module(s) 106 and the data 108 may be coupled to the processor(s) 102. The module(s) 106, amongst other things, include routines, programs, objects, components, data structures, etc., which perform particular tasks or implement particular abstract data types. The module(s) 106 may also be implemented as, signal processor(s), state machine(s), logic circuitries, and/or any other device or component that manipulate signals based on operational instructions.

In an implementation, the module(s) 106 include a video processing module 110, a signal enhancement module 112, and other module(s) 114. The other module(s) 114 may include programs or coded instructions that supplement applications or functions performed by the device 100. Additionally, in said implementation, the data 108 includes video processing data 116, signal enhancement data 118, and other data 120. The other data 120 amongst other things, may serve as a repository for storing data that is processed, received, or generated as a result of the execution of one or more modules in the module(s) 106. Although the data 108 is shown internal to the device 100, it may be understood that the data 108 can reside in an external repository (not shown in the figure), which may be operably coupled to the device 100. Accordingly, the device 100 may be provided with interface(s) (not shown) to communicate with the external repository to obtain information from the data 108.

During operation, to commence measurement of the physiological parameter, the subject, i.e., person whose heart rate is to be measured, positions a body part 126 on a camera 128 of the device 100. In an example, the subject can position the body part 126 in contact with a lens of the camera 128, or vice-versa, while a flash light of the camera 128 is switched on. For instance, the subject can position a finger tip of his hand on the camera 128 for capturing the video. In such position, according to an implementation, a video of the body part 126 of the subject is captured using the camera 128 of the device 100. In an example, the flash light can be a light-emitting diode (LED) type of flash light and can provide appropriate illumination to the body part 126 for effectively capturing the video for further processing. In one example, the camera 128 of the device 100 can capture the video at a rate of about 30 frames per second (fps). The video captured may then be stored in the video processing data 116 of the device 100.

In an example, the video may be processed for obtaining a PPG signal based on which the physiological parameter of the subject is estimated. For instance, the video processing module 110 may divide the frames of the video into a plurality of blocks. In an example, the video processing module 110 may divide the frames in a manner such that each of the blocks is of same predetermined dimension. Further, the video processing module 110 may generate a block identifier for each of the blocks. For instance, the video processing module 110 may generate a block number for each of the blocks for identifying the blocks. In another example, the video processing module 110 may generate co-ordinates corresponding to each of the blocks. The video processing module 110 may store the block identifiers in the video processing data 116 for identification of the blocks in future.

Upon dividing the frames into blocks, the video processing module 110 may compute a PSNR for each of the blocks. The PSNR associated with a block of a frame may indicate a measure of noise component present in a region of the frame corresponding to the block. In an example, the video processing module 110 may compute the PSNRs using known conventional techniques. Further, the video processing module 110 may store the PSNRs in the video processing data 116.

Thereafter, the video processing module 110 may select a block having highest PSNR from amongst the plurality of blocks for extracting the PPG signal based on the block. In order to extract the PPG signal, the video processing module 110 may, at first, ascertain the block identifier corresponding to the block. As mentioned previously, the block identifiers are stored in the video processing data 116. For ascertaining the block identifier corresponding to the block, the video processing module 110 may access the video processing data 116 and may, subsequently, ascertain the block number corresponding to the block. The video processing module 110 may then identify a region corresponding to the block number in each of the frames of the video for extracting the PPG signal from the regions. As may be understood, the region corresponding to the block number and, in turn, the block having the highest PSNR may have high PSNR. As a result, the corresponding regions may have less noise component and thus, the PPG signal obtained from such regions may be of good quality. On identifying the regions, the video processing module 110 may extract the PPG signal from the video based on the regions.

In an implementation, the signal enhancement module 112 may enhance the PPG signal. For instance, the signal enhancement module 112 may pass the PPG signal through a filter for obtaining a filtered PPG signal. Filtering of the PPG signal reduces the noise present in the PPG signal. In an example, the filter may be an adaptive filter, such as a normalized Least Mean Square (NLMS) filter. Thereafter, the signal enhancement module 112 may apply an interpolation technique to the filtered PPG signal. Application of the interpolation techniques facilitates peak detection in frequency domain thereby, increasing the accuracy of determination of the physiological parameter. Examples of the interpolation technique may include, but are not limited to, linear interpolation and Jacobsen interpolation.

In an implementation, the device 100 may use the enhanced PPG signal, i.e., the PPG signal after enhancement, for determining the physiological parameter, for example, heart rate of the subject.

In an embodiment, while recording the video of the body part 126 of the subject, flash brightness of the camera 128 may be adjusted based on a skin tone of the individual. For instance, an intensity level of a flash of the camera 128 of the PPM device 100 to operate the camera 128 at one or more intensity levels of the flash for capturing a test video of the subject at each of the one or more intensity levels of the flash. Thereafter, for each of the one or more intensity levels of the flash, a PSNR for the test video captured at the intensity level of flash may be determined. Subsequently, a test video having highest PSNR from amongst the test videos captured at the one or more intensity levels of the flash may be determined and the video of the subject may be captured at the intensity level of flash corresponding to the test video having the highest PSNR. In an example, the video processing module 110 may adjust the flash in a manner as described above.

Figure 2:
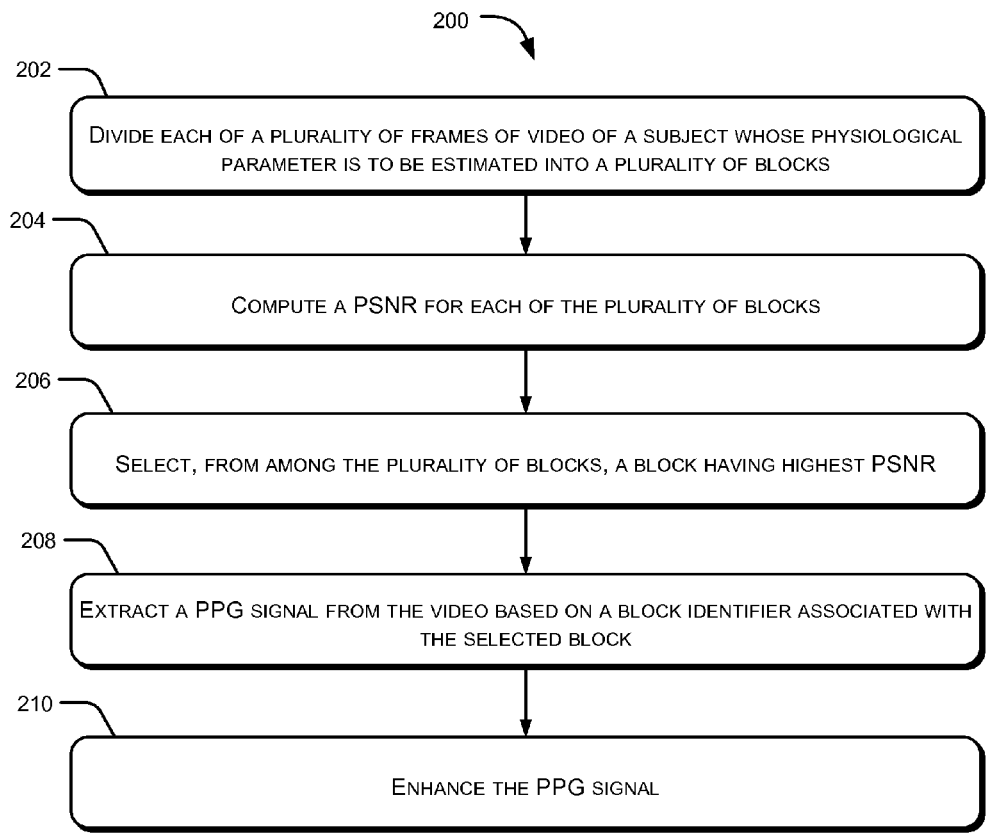
FIG. 2 illustrates a method for determining physiological parameter associated with a subject, in accordance with an implementation of the present subject matter.

FIG. 2 illustrates a method 200 for estimating physiological parameter of a subject, according to an embodiment of the present subject matter. The order in which the method 200 is described is not intended to be construed as a limitation, and any number of the described method blocks can be combined in any order to implement the method or any alternative methods. Additionally, individual blocks may be deleted from the method without departing from the spirit and scope of the subject matter described herein. Furthermore, the method can be implemented in any suitable hardware, software, firmware, or combination thereof.

The method may be described in the general context of computer executable instructions. Generally, computer executable instructions can include routines, programs, objects, components, data structures, procedures, modules, functions, etc., that perform particular functions or implement particular abstract data types. The method may also be practiced in a distributed computing environment where functions are performed by remote processing devices that are linked through a communication network. In a distributed computing environment, computer executable instructions may be located in both local and remote computer storage media, including memory storage devices.

In an implementation, one or more of the method described herein may be implemented at least in part as instructions embodied in a non-transitory computer-readable medium and executable by one or more computing devices. In general, a processor, for example, a microprocessor, receives instructions from a non-transitory computer-readable medium, for example, a memory, and executes those instructions, thereby performing one or more method, including one or more of the method described herein. Such instructions may be stored and/or transmitted using any of a variety of known computer-readable media.

Referring to FIG. 2, at block 202, each of a plurality of frames of a video of a subject whose physiological parameter is to be estimated is divided into a plurality of blocks. In an example, the vide of the subject may be a pre-recorded video, i.e., a video recorded at an instant of time prior to estimation of the physiological parameter. In another example, the video may be captured when the estimation is being done in real-time. For instance, the video may be captured using the camera 128. While capturing the video, a flash of the camera 128 may be switched on. Further, the flash brightness may be adjusted based on a skin tone of the subject. In an example, each of the blocks is of same predetermined dimension. In an implementation, the video processing module 110 may divide each of the frames into plurality of blocks.

At block 204, a PSNR for each of the blocks is computed. In an example, the video processing module 110 may compute the PSNR.

At block 206, a block having highest PSNR is selected from amongst the plurality of blocks. In an example, the PSNRs of the blocks may be analyzed for identifying the block having the highest PSNR. The block may then be selected for extraction of PPG signal.

At block 208, a PPG signal is extracted from the video based on a block identifier associated with the block. In an example, the video processing module 110 may extract the PPG signal from the video in a manner as described above in FIG. 1.

At block 210, the PPG signal is enhanced. As a part of enhancement, in an example, the PPG signal may be filtered to obtain a filtered PPG signal. Further, an interpolation technique may be applied to the filtered PPG signal for further enhancement of the PPG signal. Thereafter, on completion of the enhancement, the physiological parameter of the subject may be determined.

Although implementations for methods and systems for estimating physiological parameters are described, it is to be understood that the present subject matter is not necessarily limited to the specific features or methods described. Rather, the specific features and methods are disclosed as implementations for estimating physiological parameters.

We claim:

1. A physiological parameter measurement (PPM) device, the PPM device comprising:
   a processor;
   a video processing module coupled to the processor to,
      divide each of a plurality of frames of a video into a plurality of blocks, wherein the video is of a body part of a subject whose physiological parameter is to be determined;
      select a block, from amongst the plurality of blocks, having highest peak signal to noise ratio (PSNR);
      extract a photoplethysmogram (PPG) signal from the video based on a block identifier associated with the block, wherein the video processing module is further configured to:
         adjust an intensity level of a flash of a camera of the PPM device to operate the camera at one or more intensity levels of the flash for capturing a test video of the subject at each of the one or more intensity levels of the flash;
         for each of the one or more intensity levels of the flash, determine a PSNR for the test video captured at the intensity level of flash;
         determine, from amongst the test videos captured at the one or more intensity levels of the flash, a test video having highest PSNR; and
         capture the video of the subject at the intensity level of flash corresponding to the test video having the highest PSNR; and
   a signal enhancement module coupled to the processor to,
      enhance the PPG signal for determining a value of the physiological parameter associated with the subject.

2. The PPM device as claimed in claim 1, wherein the video processing module is further configured to compute the PSNR for each of the plurality of blocks.

3. The PPM device as claimed in claim 1, wherein the video processing module is further configured to,
   determine the block identifier associated with the block; and
   identify a region in each frame of the video based on the block identifier; and
   select the identified region corresponding to each of the frames of the video for extracting the PPG signal.

4. The PPM device as claimed in claim 1, wherein the signal enhancement module is further configured to,
   filter the PPG signal to obtain a filtered PPG signal; and
   apply an interpolation technique on the filtered PPG signal to enhance the PPG signal.

5. A method comprising:
   dividing, by a processor, each of a plurality of frames of a video into a plurality of blocks, wherein the video is of a body part of a subject whose physiological parameter is to be determined;
   selecting a block, from amongst the plurality of blocks, having highest peak signal to noise ratio (PSNR);
   extracting a photoplethysmogram (PPG) signal from the video based on a block identifier associated with the block;
   enhancing the PPG signal for determining a value of the physiological parameter for the subject;
   adjusting an intensity level of a flash of a camera to operate the camera at one or more intensity levels of the flash for capturing a test video of the subject at each of the one or more intensity levels of the flash;
   for each of the one or more intensity levels of the flash, determining a PSNR for a test video captured at the intensity level of flash;
   determining, from amongst the test videos captured at the one or more intensity levels of the flash, a test video having highest PSNR; and
   capturing the video of the subject at the intensity level of flash corresponding to the test video having the highest PSNR.

6. The method as claimed in claim 5, wherein the method further comprises computing the PSNR for each of the plurality of blocks.

7. The method as claimed in claim 5, wherein the extracting comprises:
   ascertaining the block identifier associated with the block;
   identifying a region in each frame of the video based on the block identifier; and
   selecting the region corresponding to each of the frames of the video for extracting the PPG signal.

8. The method as claimed in claim 5, wherein the enhancing the PPG signal further comprises:
   filtering the PPG signal to obtain a filtered PPG signal; and
   applying an interpolation technique on the filtered PPG signal to enhance the PPG signal.

9. The method as claimed in claim 5, wherein the physiological parameter comprises at least one of a heart rate, a blood pressure, and an oxygen saturation.

10. A non-transitory computer-readable medium having embodied thereon a computer program for executing a method comprising:
   dividing, by a processor, each of a plurality of frames of a video into a plurality of blocks, wherein the video is of a body part of a subject whose physiological parameter is to be determined;
   selecting a block, from amongst the plurality of blocks, having highest peak signal to noise ratio (PSNR);
   extracting a photoplethysmogram (PPG) signal from the video based on a block identifier associated with the block;
   enhancing the PPG signal for determining a value of the physiological parameter for the subject;
   adjusting an intensity level of a flash of a camera to operate the camera at one or more intensity levels of the flash for capturing a test video of the subject at each of the one or more intensity levels of the flash;
   for each of the one or more intensity levels of the flash, determining a PSNR for a test video captured at the intensity level of flash;
   determining, from amongst the test videos captured at the one or more intensity levels of the flash, a test video having highest PSNR; and
   capturing the video of the subject at the intensity level of flash corresponding to the test video having the highest PSNR.

11. The non-transitory computer-readable medium as claimed in claim 10, wherein the method further comprises computing the PSNR for each of the plurality of blocks.

12. The non-transitory computer-readable medium as claimed in claim 10, wherein the extracting comprises:
   ascertaining the block identifier associated with the block;
   identifying a region in each frame of the video based on the block identifier; and
   selecting the region corresponding to each of the frames of the video for extracting the PPG signal.

13. The non-transitory computer-readable medium as claimed in claim 10, wherein the enhancing the PPG signal further comprises:
   filtering the PPG signal to obtain a filtered PPG signal; and
   applying an interpolation technique on the filtered PPG signal to enhance the PPG signal.

14. The non-transitory computer-readable medium as claimed in claim 10, wherein the physiological parameter comprises at least one of a heart rate, a blood pressure, and an oxygen saturation.

* * * * *